United States Patent [19]

Billenstein et al.

[11] 4,234,509

[45] Nov. 18, 1980

[54] PROCESS FOR THE MANUFACTURE OF FATTY ACID NITRILES AND GLYCEROL FROM GLYCERIDES, ESPECIALLY FROM NATURAL FATS AND OILS

[75] Inventors: Siegfried Billenstein, Burgkirchen; Bruno Kukla, Gendorf; Herbert Stühler, Burgkirchen, all of Fed. Rep. of Germany

[73] Assignee: Hoechst Aktiengesellschaft, Fed. Rep. of Germany

[21] Appl. No.: 32,753

[22] Filed: Apr. 24, 1979

Related U.S. Application Data

[63] Continuation-in-part of Ser. No. 933,955, Aug. 15, 1978, abandoned.

[30] Foreign Application Priority Data

Aug. 20, 1977 [DE] Fed. Rep. of Germany ....... 2737607
Mar. 25, 1978 [DE] Fed. Rep. of Germany ....... 2813204

[51] Int. Cl.$^3$ ................. C07C 120/00; C07C 120/08; C07C 120/10
[52] U.S. Cl. ............................... 260/465.2; 568/852; 568/869
[58] Field of Search ...................................... 260/465.2

[56] References Cited

U.S. PATENT DOCUMENTS

| 2,037,389 | 4/1936 | Nicodemus et al. | 260/465.2 |
|---|---|---|---|
| 2,524,831 | 10/1950 | Potts | 260/465.2 X |
| 2,589,232 | 3/1952 | Drew et al. | 260/465.2 |
| 2,794,043 | 5/1957 | Jansen et al. | 260/465.2 |
| 2,808,426 | 10/1957 | Potts et al. | 260/465.2 |
| 2,993,926 | 7/1961 | Stenberg et al. | 260/465.2 |
| 3,850,974 | 11/1974 | Lichtenwalter et al. | 260/465.2 X |

FOREIGN PATENT DOCUMENTS

| 416631 | 9/1934 | United Kingdom | 260/465.2 |
|---|---|---|---|
| 451594 | 8/1936 | United Kingdom | 260/465.2 |

OTHER PUBLICATIONS

Handbook of Tables for Organic Compound Identification, 3rd Ed., Rappoport, 1967, p. 86, The Chem. Rubber Co.
Hauschild et al., C. A., 50, 1958, 14243-f.
Ullmanns Encyklopodie der Technischen Chemie, 4th Ed., 1976, vol. 12, pp. 367-368.

*Primary Examiner*—Joseph Paul Brust
*Attorney, Agent, or Firm*—Connolly and Hutz

[57] ABSTRACT

Glycerol and aliphatic nitriles are simultaneously produced by treating liquid glycerides with gaseous ammonia at a rate of at least 200 liters of ammonia per kilogram of glyceride per hour at temperatures of from 220° to 300° C. in the presence of metal salts of carboxylic or sulfonic acids as catalysts and subjecting the product mixture to a phase separation into a nitrile phase and a glycerol/water phase. Preferred starting materials are vegetable and animal fats and oils.

9 Claims, No Drawings

PROCESS FOR THE MANUFACTURE OF FATTY ACID NITRILES AND GLYCEROL FROM GLYCERIDES, ESPECIALLY FROM NATURAL FATS AND OILS

This is a continuation-in-part application of application Ser. No. 933,955 filed Aug. 15, 1978 now abandoned.

This invention relates to a process for reacting glycerides

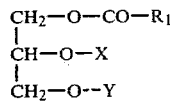

wherein X is H or CO—$R_2$, and Y is H or CO—$R_3$, or mixtures of glycerides in the liquid phase with ammonia to yield fatty acid nitriles and glycerol by passing through gaseous ammonia at elevated temperatures and in the presence of catalysts.

Fatty acid nitriles, which are important intermediates for the manufacture of amines, are produced by industrial processes, preferably from the corresponding fatty acids and ammonia in the presence of suitable catalysts. This synthesis, which has been known for quite a while, can be carried out in the liquid phase at a temperature in the range of from 250° to 350° C. as well as in the gaseous phase at a temperature of from 320° to 380° C. Suitable catalysts for the reaction in the liquid phase are, for example, zinc oxide and manganese acetate, for the gaseous phase aluminum oxide or bleaching earth have been proposed. Detailed information about the aforesaid processes are found in "Methoden der Organischen Chemie" Houben-Weyl, volume 8, pages 330 et seq., Georg Thieme Verlag, Stuttgart, 1952, and in "Fatty Acids and their Industrial Applications", Marcel Dekker, New York, 1968, pages 909 et seq. U.S. Pat. No. 2,589,232 describes a process for the manufacture of fatty acid nitriles by reaction of fatty acids with ammonia in the liquid phase in the presence of zinc or calcium salts of fatty acids. Another process in which titanic acid esters of short-chain aliphatic alcohols are used as catalysts and, besides fatty acids, the fatty acid esters of monohydric alcohols can be used as starting materials is described in U.S. Pat. No. 2,993,926. When, in the aforesaid processes, natural fats or oils are used, the free fatty acid or the ester must be obtained first in a separate stage.

It has also been proposed to react natural fats or fatty acid esters of monohydric alcohols by reaction with ammonia and to obtain in this manner the corresponding fatty acid amides. Suitable catalysts in this process are, for example, metal oxides or calcium nitrate (cf. Japanese Patent Publications No. 70-35524 and 71-21846 and Japanese Patent Application No. 71-6614). The fatty acid amides can then be transformed in known manner into the fatty acid nitriles by dehydration in a second stage.

Japanese Patent Publication No. 72-26921 proposes a process according to which natural fats can be transformed into fatty acid amides by reaction with aliphatic amines, and the glycerol formed is removed from the equilibrium as glycerol boric acid ester by the use of boric acid.

It would be desirable for economical reasons to dispose of a process in which natural fats or oils, i.e. native triglycerides, that may contain minor amounts of mono- or diglycerides, are directly transformed into the corresponding fatty acid nitriles without isolation of reaction intermediates as fatty acid amides, fatty acids or short-chain fatty acid esters.

Attempts of this kind have already been made. British Pat. Nos. 416,631 and 451,594 disclose a process for reacting hydroxy fatty acids or fatty acids, obtained from natural fats, with ammonia to obtain fatty acid nitriles, in the gaseous phase at a temperature of from 300° to 450° C. in the presence of oxidic dehydration catalysts, preferably aluminum oxide. In the specifications it is disclosed that the glycerides may be used directly although they cannot be evaporated unter the specific conditions. In Example 3 of GB-PS No. 416,631 and in Examples 7 and 14 of GB-PS No. 451,594 reactions of castor oil, palm nut fat and coconut oil with ammonia at temperatures of from 350° to 400° C. in the presence of bauxite are described, but nothing is said about the isolation of glycerol. Experiments show that under the conditions of the said process, the glycerol is completely decomposed by thermal splitting. Hence, a valuable material is lost and moreover, the quality of the fatty acid nitriles obtained is noticeably impaired, especially as regards color and odor. Fatty acid nitriles constitute intermediates and for further processing high degrees of purity are required; consequently expensive purifying procedures are necessary to remove the decomposition products, so that the above process becomes completely uneconomic.

It is therefore, one object of the present invention to provide a process by which it is possible in a single operation to produce fatty acid nitriles as well as glycerol in high yield and qualitiy and in an economic reaction time from glycerides.

This is achieved in accordance with the invention by a process for producing simultaneously glycerol and saturated or olefinically unsaturated aliphatic nitriles without isolating intermediates by treating glycerides or mixtures of glycerides with gaseous ammonia at elevated temperatures in the presence of catalysts, wherein the improvement comprises contacting the liquid glyceride at temperatures of from about 220° to about 300° C. with a flow of at least 200 liters ammonia per kilogram of glyceride per hour in the presence of metal salt of a carboxylic or sulfonic acid as a catalyst, wherein in said metal salt the metal cation is lead, cadmium, iron, cobalt, zinc tin, titanium, zirconium, chromium, antimony, manganese, or nickel and the anion is selected from the groups consisting of saturated aliphatic mono- and polycarboxylic acids; olefinically unsaturated aliphatic mono- and polycarboxylic acids; mono-, di- and trialkylated benzene and naphthalene mono- and polycarboxylic acids, alkane mono- and disulfonic acids; fluoro- and monohydroxy-substituted alkane monosulfonic acids; mono-, di- and trialkylated benzene and naphthalene mono- and polysulfonic acids; and (monocarboxy)alkyl and (dicarboxy)alkyl benzene and naphthalene mono- and polysulfonic acids or mixtures of said catalysts removing a product mixture containing said nitriles, glycerol, and water formed from the liquid glycerides, and subjecting the product mixture to a phase separation into a nitrile phase and a glycerol/water phase.

Suitable starting materials in the process of the invention are mono-, di- and triglycerides of the formulae

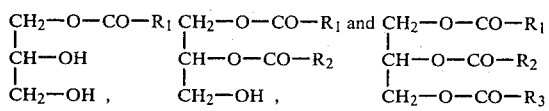

(structural isomers included) or mixtures thereof, yielding nitriles of the formulae R—CN, $R_2$—CN, and $R_3$—CN.

In these formulae $R_1$ and $R_2$ or $R_1$, $R_2$, and $R_3$ may be identical or different in the case of di- and triglycerides. The radicals $R_1$, $R_2$, and $R_3$ are selected from the following groups:

(a) Alkyl radicals which can be branched, but preferably have a straigth-chain, having from 3 to 23, preferably from 7 to 23 C atoms;

(b) olefinically unsaturated aliphatic hydrocarbon radicals, which can be branched, but preferably have a straight-chain, having from 3 to 23, preferably 11 to 21, and especially from 15 to 21 C atoms, and containing from 1 to 6, preferably from 1 to 3 double bonds, which are conjugated or isolated;

(c) monohydroxy-substituted radicals of type (a) and (b), preferably olefinically unsaturated olefinic radicals having from 1 to 3 double bonds, and particularly the chain radical of ricinoleic acid.

The acyl radicals $R_1$—CO—, $R_2$—CO—, and $R_3$—CO— of such glycerides, suitable as starting materials in the process of the present invention, are derived from the following groups of aliphatic carboxylic acids (fatty acids):

(a) Alkanoic acids and alkyl-branched, especially methylbranched, alkanoic acids, having from 4 to 24 carbon atoms, as for example, butyric, valeric, caproic, heptylic, caprylic, pelargonic, capric, undecylic, lauric, tridecylic, myristic, pentadecylic, palmitic, margaric, stearic, nonadecylic, arachidic, behenic, lignoceric, 2-methylbutanoic, isobutyric, isovaleric, pivalic, isocaproic, 2-ethylcaproic, 2-methylcapric, 3-methylcapric, 4-methylcapric, 5-methylcapric, 6-methylcapric, 7-methylcapric, 9-methylcapric, 2-methyllauric, 3-methyllauric, 2-methylstearic, 3-methylstearic, 4-methylstearic, 5-methylstearic, 6-methylstearic, 7-methylstearic, 8-methylstearic, 9-methylstearic, 10-methylstearic, 11-methylstearic, 14-methylstearic, 15-methylstearic, 16-methylstearic, 17-methylstearic, 12-hexylstearic, isostearic, or 3,3-dimethylstearic acid.

(b) alkenoic, alkadienoic, alkatrienoic, alkatetraenoic, alkapentaenoic, and aikahexaenoic acids and their alkyl-branched, especially methyl-branched derivatives having from 4 to 24 carbon atoms, as for example, crotonic, isocrotonic, caproleic, linderic, 3-lauroleic, myristoleic, palmitoleic, petroselinic, oleic, elaidic, erucic, brassidic, 2,4-decadienoic, linoleic, 11,14-eicosadienoic, hiragonic, eleostearic, linolenic, pseudoeleosteraric, arachidonic, 4,8-12,15-18,21-tetracosahexaenoic or trans-2-methyl-2-butenoic acid, (c) monohydroxyalkanoic acids having from 4 to 24, preferably from 12 to 24 carbon atoms, and preferably unbranched, as for example, hydroxybutyric, hydroxyvaleric, hydroxycaproic, 2-hydroxydodecanoic, 2-hydroxytetradecanoic, 15-hydroxypentadecanoic, 16-hydroxyhexadecanoic, hydroxyoctadecanoic acid, and (d) monohydroxyalkenoic acids having from 4 to 24, preferably from 12 to 22 and more preferably from 16 to 22 carbon atoms (preferably unbranched) and from 1 to 6, preferably from 1 to 3, and more preferably 1 ethylenic double bonds, as for example, ambrettolic, ricinoleic, ricinelaidic or kamalenic acid.

Preferred starting materials in the process of the invention are the naturally occurring vegetable or animal fats and oils containing a preponderant proportion of triglycerides and smaller proportions of diglycerides and monoglycerides, the amount of the latter being dependent on the degree of purification. Edible fats which may also be used are most frequently pure triglycerides. The diglycerides and triglycerides may contain different fatty acid radicals within the limits described before. There are mentioned, by way of example, vegetable fats and oils such as olive oil, coconut oil, palm kernel fat, babassu oil, palm oil, peanut oil, rape oil, castor oil, sesame oil, sunflower oil, soybean oil, hempseed oil, poppy oil, avocado oil, cotton seed oil, wheat germ oil, maize germ oil, pumpkin seed oil, grapeseed oil, coconut oil and vegetable tallows; furthermore animal fats and oils such as beef tallow, lard, bone fat, mutton tallow, Japan tallow, grease whale oil, sardine oil, shark oil and other fish oils, and cod liver oil.

In the process of the invention it is likewise possible to use as starting material pure tri-, di- and mono-glycerides or mixtures thereof either isolated from natural fats or synthetized, preferably those with identical fatty acid acyl radicals, for example tributyrin, tricapronin, tricaprylin, tricaprinin, trilaurin, trimyristin, tripalmitin, tristearin, triolein, trielaidin, trilinoliin, trilinolenin, monopalmitin, monostearin, monoolein, monocaprinin, monolaurin, monomyristin, but also synthetic glycerides with different acyl radicals, such as palmitodistearin, distearoolein, dipalmitoolein and myristopalmitostearin.

Decisive for the success of the one-stage process of the invention, i.e. the production of fatty acid nitrile or of a mixture of fatty acid nitriles in a high purity and high yield with the simultaneous production of glycerol in a high yield are, above all, three process parameters, namely the selection of the appropriate reaction temperature or temperature conditions, the rapid removal of the glycerol formed from the reaction zone and the selection of the catalyst.

To ensure a rapid removal of the glycerol from the reaction zone a minimum amount of at least 200 liters of ammonia should be passed through the reaction mixture per kilogram of glyceride per hour, preferably at least 400 liters per kilogram of glyceride per hour. As regards the ammonia current to be passed through there is no critical upper limit, but economical considerations will limit the amount of ammonia to about 1,000 liters, preferably 800 liters per kilogram of glyceride per hour. It proved advantageous to add to the gaseous ammonia up to 30% and advantageously up to 15%, calculated on the amount of ammonia passed through, of an inert gas, for example nitrogen.

Furthermore, in the process of the invention it is very important that the reaction temperature during the entire course of the reaction is maintained in the range of from 220° to 300° C., preferably 230° to 290° C. It proved advantageous to allow the temperature to rise from the beginning to the end of the process, either continuously or gradually according to a temperature program. According to a preferred embodiment, the reaction is carried out at a temperature between 220° and about 240° C. until about 30 to 70% of the amount of glycerol to be expected theoretically are discharged from the reaction vessel, the temperature is then raised, during the course of about 30 minutes to 5 hours, either gradually or continuously, to about 270° to 300° C., whereupon the reaction is completed within the latter temperature range. The reaction is complete when no more liquid phase passes into the receiver.

Finally, the selection of the catalyst is of decisive importance to the process of the invention. Suitable catalysts are metal salts of an aliphatic or aromatic sulfonic or carboxylic acid. In said metal salts the metal cation is tin, titanium, zirconium, chromium, antimony, manganese, nickel, preferably lead, cadmium, iron, cobalt, and particularly zinc. The carboxylic or sulfonic acid anion is taken from the following groups:

(a) saturated aliphatic poly- and preferably monocarboxylic acids (alkanoic and alkan-polyoic acids), which can be branched or straight, containing from 4 to 24, preferably from 8 to 24 carbon atoms;

(b) olefinically unsaturated aliphatic monocarboxylic acids having from 1 to 6, preferably from 1 to 3, isolated or conjugated double bonds (alkenoic and alkapoly-enoic acids, especially alkadienoic and alkatrienoic acids), which can be branched, but preferably are straightchain, containing from 4 to 24, preferably from 8 to 24 carbon atoms;

(c) trialkylated and particularly dialkylated and monoalkylated benzene and naphthalene carboxylic acids having from 1 to 3, preferably 1 COOH group, and alkyl radicals with from 1 to 23, preferably from 1 to 12 carbon atoms, said alkyl radicals are branched or preferably straight-chained;

(d) alkanedisulfonic and preferably alkanemonosulfonic acids, furthermore, monohydroxy-alkanemonosulfonic acids, fluoro-substituted alkanemonosulfonic acids (preferably perfluoro-substituted); all of them can be branched, but preferably are straight, and contain from 4 to 24, preferably from 8 to 24, carbon atoms and (e) trialkylated, and particularly dialkylated and monoalkylated benzene and naphthalene sulfonic acids, having from 1 to 3, preferably from 1 to 2 $SO_3H$ groups, and alkyl radicals with from 1 to 24, preferably from 1 to 12 carbon atoms, said alkyl radicals can be branched or straight and may be substituted by 2, preferably 1 COOH group.

The metal salts of alkyl benzene and naphthalene sulfonic acids of group (d) and (e) are particularly suitable.

From the above-mentioned groups of acids, from which the anions of the metal salts are derived, the following are mentioned by way of example: fatty acids as stearic, caprylic, myristic, palmitic, isopalmitic, erucic, oleic and tallow fatty acid; alkylarene carboxylic acids as methyl benzoic acids (toluic acids), n-dodecylbenzoic acid, methyl naphthoic acids, n-dodecyl naphtholic acid, alkanesulfonic acids as n-octanesulfonic acid, pentadecanesulfonic acid, hexadecanesulfonic acid, heptadecanesulfonic acid, octadecanesulfonic acid, perfluorohexanesulfonic acid, β-hydroxydodecanesulfonic acid; alkylarenesulfonic acids as toluenesulfonic acid, isopropylnaphthalenesulfonic acid, toluene-2,4-disulfonic acid, 2.5-dimethylbenzenesulfonic acid, octadecylbenzenesulfonic acid, and particularly n-dodecylbenzenesulfonic acid; furthermore, reaction products of benzene or naphthalene with alkenoic acids such as oleic acid, sulfonated with oleum, which contain branched-alkylated benzene- or naphthalenesulfonic acids, the alkyl being substituted with 1 or 2 COOH groups.

All possible mixtures of such metal salt catalysts can be used, particularly those of the same group of homologues of anions.

The salt to be used as catalysts in the process of the invention can be prepared by reacting the free acids with the corresponding metal oxides by known methods. The free sulfonic acids can be obtained by known sulfonation processes or from the corresponding alkali metal sulfonates, for example with the help of ion exchangers. The aforesaid catalysts can be added directly in salt form. Alternatively, the respective metal oxide and the carboxylic acid or sulfonic acid can be added separately to the reaction mixture, whereupon the catalyst is formed in situ during the course of the reaction. In the process of the invention the aforesaid catalysts are added in an amount of from 0.5 to 75% by weight, with a discontinuous operation preferably in an amount of from 1 to 25% by weight, more preferably 1 to 10% by weight, and with a continuous operation preferably in an amount of from 5 to 75% by weight, more preferably 10 to 30% by weight, the percentages being calculated on the glyceride used.

To carry out the process of the invention the reaction vessel, for example a vessel stirrer, is charged with the glyceride or glyceride mixture and the catalyst. The total amount of the catalyst can be added at the beginning or a partial amount thereof and the remainder is then added in portions or continuously during the course of the reaction. The reaction vessel is provided with an equipment for gas inlet by which the flow of gas can be measured, a temperature measuring device, heating means and optionally with a stirrer. The reaction vessel is connected with a condensation apparatus consisting of one or preferably several (up to 6) receivers heated to about 60° to 120° C. After heating of the reaction vessel, optionally under nitrogen, and when the reaction temperature has been reached, ammonia is introduced. At the beginning, the product mixture collected in the condensation apparatus contains a higher proportion of crude glycerol. During the course of the reaction the proportion of fatty acid nitrile increases gradually and, towards the end of the reaction, substantially pure fatty acid nitrile is collected while the discharge of crude glycerol has ceased previously. The ammonia current (to which inert gas may be added as mentioned above) further ensures a rapid removal of the reaction water over the entire reaction period. After separation of the entrained water and optionally with the addition of fresh ammonia, the issuing gas current is recycled into the reaction. The discharged product mixture is collected in the condensation apparatus and separated into a fatty acid nitrile phase and a crude glycerol/water phase. The final phase separation is expediently carried out after discharge from the condensation apparatus and transfer into a separator, for example a vapor separator, at about 60° to 100° C. Residual glycerol is washed out of the fatty acid nitrile phase by means of water. The crude glycerol isolated from the aqueous phase, for example by distillation, can be purified by known methods (cf. Ullman "Encyklopä die der Technischen Chemie" 1965, volume 7, pages 523 to 524), for example by distillation.

By the process of the invention it is possible to produce fatty acid nitriles and glycerol in excellent yields of up to 93%, in many cases up to 96% and more of fatty acid nitrile and up to 95% of crude glycerol, each time calculated on the theoretical yield on the basis of the glyceride used. The fatty acid nitrile obtained contains at most 2% by weight of free fatty acids and up to 15%, in most cases, however, less than 6%, of fatty acid amides as by-products.

It is another object of the invention to transform these minor amounts of free fatty acids and fatty acid amides, contained in the discharged product mixture, into fatty acid nitriles by subjecting the mixture, after or optionally prior to the phase separation, to an after-reaction in the presence of ammonia and of the catalysts specified above.

To this after-reaction there can be subjected either the free fatty acids and fatty acid amides separated from the discharged fatty acid nitrile, optionally together with crude nitrile not yet discharged, or the whole fatty acid nitrile phase. In the following are described methods to carry out the after-treatment.

According to a preferred method a fractionation column is intercalated between the reactor and the condensation apparatus. In this column, which may be a mirror glass column or a well isolated tube, filled, for example with Raschig rings, the fatty acid amides and free fatty acids, which are reaction intermediates, are separated by fractionated distillation and recycled into the reaction vessel, while the remaining product mixture passes into the receiver where it is collected with condensation as described above.

With the intercalation of the fractionation system, the process of the invention can be performed fully continuously in an especially simple manner. To this end, the glyceride as defined above is first introduced into the reaction vessel together with the specified amount of catalyst or it is added in dosed quantities to an inert, non volatile solvent, for example paraffin oil, in the reaction vessel. The amount of ammonia to be introduced into the continuous process is at least 200 liters per kilogram of glyceride per hour, but normally higher amounts than indicated above for a discontinuous operation are passed through.

The temperatures of the continuous process are advantageously in the range of from 220° to 270° C., preferably 230° to 250° C. During the reaction, the glyceride is continuously metered in. It is likewise possible to add continually a mixture of the glyceride with the catalyst. Fatty acid nitrile, glycerol and water are constantly discharged through the fractionation system while fatty acid amide and free fatty acid are continually recycled into the process.

According to another variant of the after-treatment the reaction is continued until substantially the entire amount of the crude glycerol is discharged (what is indicated in the step of phase separation, when the phase of crude glycerol does no longer increase). With the crude glycerol a portion (50 to 80% of theoretical amount) of proportional amounts of nitrile and water is discharged. The fatty acid nitrile phase resulting from the phase separation is recycled into the reactor, preferably after washing with water, and combined with the portion of fatty acid nitrile not yet discharged, in the reactor a temperature in the range of from 200° to 230° C. is adjusted and the flow of ammonia is reduced to from 5 to 150 liters/kg of fatty acid nitrile per hour, preferably to from 15 to 100 liters per kilogram per hour. If in the first stage of the reaction a sufficient amount of catalyst has been added (amount at the upper limit of the indicated range) fresh catalyst need not be added. Otherwise, an appropriate amount of catalyst should be added. Under these reaction conditions the fatty acid amides and fatty acids are quantitatively transformed into fatty acid nitriles, as can be ascertained by the formation of reaction water. This water is discharged together with the excess amount of ammonia, the water is separated and the ammonia is recycled, optionally with the addition of fresh ammonia. When the reaction is complete, the fatty acid nitrile in the reactor is suitably distilled to remove the catalyst.

Alternatively, the entire amount of fatty acid nitrile can be removed from the reactor, subjected to phase separation and then introduced into a second reactor (after-reactor) into which a catalyst is introduced as defined above. The after-treatment is carried out unter the same conditions as the above process wherein a partial amount is recycled into reaction vessel. In this case too, the fatty acid nitrile should be worked up by distillation after termination of the after-treatment.

The latter method can be modified in a manner such that the entire fatty acid nitrile phase is conducted continuously under the described conditions, for example through a tube reactor, wherein the after-treatment is performed.

Finally, the fatty acid nitrile phase obtained can be passed continuously over a fixed bed dehydration catalyst together with ammonia in an amount of 200 to 800 liters per kilogram of fatty acid nitrile per hour, preferably 300 to 600 liters per kilogram per hour, at a temperature of from 280° to 400° C., preferably 300° to 380° C. Suitable dehydration catalysts are, for example, aluminum oxide in the form of bauxite or hydrargillite, thorium oxide, zirconium oxide, aluminum phosphate, silica gel, active bleaching earth and the like, and mixtures thereof.

Surprisingly, the process of the invention makes it possible to produce not only fatty acid nitriles but also glycerol in excellent yields and in high purity. By the after-treatment methods as described above the purity of the fatty acid nitrile is further improved so that it finally contains less than 5% by weight, in most cases less than 0.1% by weight of fatty acid amide and less than 1.5% by weight and in most cases less than 0.1% by weight of free fatty acid and is free from other by-products.

Fatty acid nitriles are important chemical intermediates, especially for the manufacture of primary amines and quaternary ammonium salts, which, for their part, are mainly used as textile auxiliaries, flotation auxiliaries and cation-active surfactants in many industrial processes. Gylcerol is an important chemical compound, for example for the manufacture of explosives, as additive for heat- and force-transmitting fluids, as moisture-conserving additive to skin creams, tooth pastes, soaps, tobacco and the like, as textile auxiliary, as solvent and in many other fields known to everybody skilled in the art.

The following examples illustrate the invention.

EXAMPLE 1

The reaction was carried out in a heatable reactor having a capacity of 800 cc and provided with gas inlet, stirrer, internal thermometer and fractionation column in the form of a glass tube (length 20 cm, diameter 1.5 cm) filled with Raschig rings and a receiver system of three series-connected receivers in which the volatile reaction products were condensed. The reactor was charged with 495 g of tallow (saponification number 190, acid number 7.6) and 5 g of zinc dodecylbenzenesulfonate as catalyst. During heating the reactor was scavenged with nitrogen. The nitrogen was then replaced by gaseous ammonia which was conducted in a cycle in an amount of 600 l of NH$_3$ per kilogram of tallow per hour. During the reaction fresh gaseous ammonia was constantly added. The temperature in the reactor was as follows:

| reaction time (hr) | temperature in reactor |
|---|---|
| 3 | 230° C. |
| 0.75 | 230→250° C. |
| 0.25 | 230→260° C. |
| 0.25 | 260 270° C. |
| 1 | 270° C. |
| 0.5 | 270→290° C. |
| 1.25 | 290° C. |

The reaction of the tallow with ammonia was complete after a total reaction time of 7 hours. The tallow nitrile and glycerol were collected in 2 series-connected receivers, while in another receiver ammoniacal reaction water was condensed.

The glycerol and tallow nitrile collected as two phases in the two first receivers were separated and the tallow nitrile was washed with water. 413.7 g (93.6%) of tallow nitrile having an amide content of 1.8% and a tallow fatty acid content of 1.5% by weight and 39.6 g (80.2%) of pure glycerol were obtained after working up. (The yields given in parentheses here and in the following are calculated on the theoretical yield based on starting glyceride.)

EXAMPLE 2

The apparatus as described in Example 1, was charged with 495 g of beef tallow (saponification number 190, acid number 1.6) and 10 g of zinc dodecylbenzenesulfonate and, starting at 230° C., 600 l of NH$_3$ per kilogram of beef tallow per hour were passed through. The following temperature conditions were maintained in the reactor:

| reaction time | temperature in reactor |
|---|---|
| 30 min | 230° C. |
| 20 min | 235° C. |
| 20 min | 240° C. |
| 20 min | 245° C. |
| 1 h 10 min | 250° C. |
| 1 h 20 min | 255° C. |
| 30 min | 260° C. |
| 60 min | 270° C. |
| 60 min | 280° C. |
| 60 min | 290° C. |

The total reaction time was 7.5 hours. The reaction products collected in the receivers were washed out with water and worked up. 408 g (92.3%) of tallow nitrile having an amide content of 0.7% by weight and a fatty acid content of 0.5% by weight and 44.7 g (87.7%) of crude glycerol were obtained. The isolated crude glycerol contained, according to the hydroxyl number of 1694, 81.2% of glycerol, calculated on the tallow used.

EXAMPLE 3

The apparatus described in Example 1 was charged with 445 g of industrial grade tallow (bleachable tallow, saponification number 186, acid number 12.6) and 9 g of zinc dodecylbenzenesulfonate and the mixture was reacted with ammonia under the conditions of Example 2. The reaction products discharged during the reaction over a period of 7.5 hours were combined and the glycerol was washed out with water. After separation of the aqueous phase, 370.4 g (93.0%) of tallow nitrile having an amide content of 0.5% by weight and a fatty acid content of 0.3% by weight could be isolated. Crude glycerol was obtained from the aqueous phase in a yield of 38.5 g (91.3%). According to the OH number, the yield of pure glycerol amounted to 84.0%, calculated on the tallow used.

EXAMPLE 4

The apparatus as described in Example 1 and additionally provided with a 70 cm mirror glass column filled with Raschig rings for fractionation was charged with 488 g of edible tallow (saponification number 190, acid number 2.4) and 5 g of zinc toluenesulfonate. During heating a weak nitrogen current was passed through the reactor. At 190° C., the nitrogen was replaced by 600 l of NH$_3$ per kilogram of fat per hour. The reaction was continued for 3 hours at 230° C. The temperature was then raised from 230° to 270° C. within 30 minutes and maintained at the higher level for a further 3.25 hours. After a total period of 6.75 hours all volatile reaction products from the reactor had passed the column. The mixture of glycerol and tallow nitrile collected in the receiver system was treated with water and, after working up of the two phases, tallow nitrile was obtained in a yield of 406 g (93.2%) (1.7% of amide and 0.5% by weight of fatty acid) and pure glycerol was obtained in a yield of 40.1 g (80.1%).

In the same apparatus and under the same conditions edible tallow was reacted in the presence of other catalysts. In the following table the test results are summarized.

| catalyst | reaction time (hr) | nitrile yield (%) | amide content (% b.w.) | yield of pure glycerol (%) |
|---|---|---|---|---|
| 1% b.w. of zinc perfluorohexane-sulfonat | 6.25 | 93.8 | 0.9 | 78 |
| 1% b.w. of zinc isopropylnaphthalenesulfonate | 7 | 94 | 1.3 | 82 |
| 1% b.w. of zinc C$_{15}$/C$_{18}$- alkanesulfonate | 6.75 | 94 | 2 | 83 |
| 1% b.w. of zinc salt of the reaction product of benzene, oleic acid and H$_2$SO$_4$ (alkylbenzenesulfonic acid carrying a carboxyl group in the alkyl chain) | 6 | 92 | 0.7 | 77 |

EXAMPLE 5

In the apparatus as described in Example 4, 436 g of sunflower oil (saponification number 189, acid number 0.8) and 9 g of zinc dodecylbenzenesulfonate as catalyst were reacted under the conditions of Example 4 (reaction time 6.75 hours) with gaseous ammonia (690 liters per kilogram of fat per hour. After working up, there were obtained 94.6% of fatty nitrile (amide content 0.5% by weigth, fatty acid content 0.35% by weight) and 91.2% of crude glycerol (40.9 g) or 85.6% of pure glycerol according to the OH number of 1717, calculated on the oil used.

EXAMPLE 6

This example is intended to demonstrate the preparation of fatty acid nitrile and glycerol directly from glyceridin in continuous operation. A heatable, cylindrical, 750 cc glass vessel was charged with 192 g of edible tallow and 7.5 g of zinc dodecylbenzenesulfonate. The reactor was provided with stirrer, internal thermometer, heated dropping funnel and 70 cm mirror glass column filled with Raschig rings. 600 l of ammonia per kilogram of fat per hour were introduced into the reactor from below at 230° C. by means of a frit. Under these conditions, 1009 g of edible tallow mixed with 1% by weight of zinc dodecylbenzene-sulfonate were added in dosed quantities over a period of 36 hours (27 to 29 g of tallow per hour). The volatile reaction products permanently discharged through the column were condensed in a receiver system. The tallow nitrile obtained was freed from glycerol by means of water. 1033 g (96.1%) of tallow nitrile (amide content 1.4% by weight) could be isolated. 115.4 g (95.5%) of crude glycerol were isolated from the water.

EXAMPLE 7

The apparatus described in Example 4 was charged with 486 g of edible tallow (saponification number 190, acid number 1.6) and 5 g of zinc dodecylbenzenesulfonate. at about 270° C., 500 l of $NH_3$ kilogram of fat per hour were passed through the reaction mixture at a constant speed. The reaction time was 6.5 hours. The reaction products collected in the receivers were washed with water and worked up. 406 g (93.7%) of tallow nitrile having an amide content of 2.2% by weight and a fatty acid content of 0.4% by weight and 36.8 g (73.45%) of pure glycerol, calculated on the tallow used, were obtained.

EXAMPLE 8

The apparatus described in Example 4 was charged with 486 g of tallow (saponification number 187.5, acid number 11.1) and 4.25 g of the zinc salt of tallow fatty acid. During heating, 30 l of $N_2$/hr were passed through the reactor and at 190° C. the nitrogen was replaced by 600 l of $NH_3$ per kilogram of fat per hour. The reaction was complete after 13 hours. During the reaction the temperature was maintained for 3 hours at 230° C. and then for 9.5 hours at 270° C. The reaction products collected in the receivers and discharged from the reactor were washed with water. 367.8 g (84.6%) of tallow nitrile and 28.3 g (60.4%) of pure glycerol were obtained, calculated on the tallow used.

EXAMPLE 9

The apparatus described in Example 1 and provided with the fractionation system of Example 4 was charged with 445 g of beef tallow (saponification number 186, acid number 0.8) and 9 g of iron-dodecylbenzenesulfonate as catalyst. Starting at 230° C., 600 l of $NH_3$ per kilogram of fat per hour were passed through the tallow. The temperature was raised to 290° C. within 7.25 hours. At the end of the reaction and after working up 364.1 g (91.4%) of tallow nitrile having an amide content of 2.9% by weight and a fatty acid content of 0.4% by weight and 30.2 g (67.0%) of pure glycerol were obtained, calculated on the tallow used.

EXAMPLE 10

The apparatus described in Example 1 was charged with 445 g of beef tallow (saponification number 190, acid number 0.2) and 9 g of lead dodecylbenzenesulfonate and, starting at 230° C., 600 l of $NH_3$ per kilogram of fat per hour were passed through. The reaction temperature was raised to 290° C. within 7.25 hours. At the end of the reaction and after working up, 350.5 g (88.2%) of nitrile having an amide content of 2.7% by weight and a fatty acid content of 0.35% by weigth and 36.5 g (78.9%) of pure glycerol were obtained.

EXAMPLE 11

The apparatus described in Example 1 was charged with 445 g of soybean oil (saponification number 203.2) an 9 g of zinc dodecylbenzenesulfonate. Starting at 230° C., 600 l of $NH_3$ per kilogram of fat per hour were passed through the oil. The reaction temperature was raised to 290° C. within 7.25 hours. At the end of the reaction and after working up, 363.3 g (92.2%) of soya nitrile having an amide content of 0.7% by weight and a fatty acid content of 0.7% by weight and 36.0 g (72.8%) of pure glycerol were obtained, calculated on the oil used.

EXAMPLE 12

The apparatus described in Example 1 was charged with 445 g of beef tallow (saponification number 192, acid number 0.25) and 9 g of cadmium dodecylbenzenesulfonate. Starting at 230° C., 600 l of $NH_3$ per kilogram of fat per hour were passed through the fat. The reaction temperature was raised to 290° C. within 6.5 hours. At the end of the reaction and after working up, 373.6 g (94.2%) of tallow nitrile having an amide content of 2% by weight and a fatty acid content of 0.7% by weight and 35.1 g (75.2%) of pure glycerol were obtained.

EXAMPLE 13

The apparatus described in Example 1 was charged with 445 g of beef tallow (saponification number 192) and 9 g of cobalt dodecylbenzenesulfonate. Starting at 230° C., 600 l of $NH_3$ per kilogram of fat per hour were passed through the fat. The reaction temperature was raised to 290° C. within 7.25 hours. At the end of the reaction and after working up, 373 g (94%) of tallow nitrile having an amide content of 4.9% by weight and a fatty acid content of 0.8% by weight and 40.3 g (86.4%) of crude glycerol were obtained.

EXAMPLE 14

The apparatus described in Example 1 which, instead of fractionation system, was provided with a direct transition pipe from the reactor to the receiver system, was charged with 486 g of edible tallow (saponification number 187, acid number 0.8) and 1% by weight of zinc dodecylbenzenesulfonate, calculated on the tallow. During the reaction 600 l of $NH_3$ per kilogram of fat per hour were passed through the reaction mixture. The temperature was maintained for 3 hours at 230° C., and after temperature increase (0.5 hr) for 1.25 hours at 270° C. After a total period of 4.75 hours, the reaction was terminated. The reaction products discharged at 230° C.

and at 270° C. were collected separately and worked up. The fatty acid nitrile isolated at 230° C. had an amide content of 20% by weight, while the amide content of the product discharged at 270° C. was found to be 9% by weight. The amide content in the total amount of fatty acid nitrile was 10% by weight.

EXAMPLE 15

The apparatus described in Example 1 which, instead of the fractionation system, was provided with a direct connecting pipe from the reactor to the receiver system, was charged with 500 g of tallow (saponification number 189, acid number 0.9) and 2% by weight of zinc dodecylbenzenesulfonate, calculated on the tallow. During the reaction 600 l of $NH_3$ per kilogram of fat per hour were passed through the reaction mixture. The temperature was maintained for 3 hours at 230° C., then raised by 10 centigrades and after every 30 minutes for a further 10 centigrades. The reaction was complete at 280° C. after a reaction time of 5.25 hours. The condensate was separated by means of water and at 80° C. into fatty acid nitrile and glycerol/water. The isolated fatty acid nitrile had an amide content of 5.3% by weight and a fatty acid content of 0.5% by weight. The nitrile yield was 95.2%. After working up, 91.4% of pure glycerol were obtained.

EXAMPLE 16

A heatable reactor equipped with gas inlet tube, stirrer and internal thermometer and connected with a receiver system (condensation system of one or several receivers and containers) was charged with 500 g of industrial grade tallow (saponification number 191.4, acid number 1.5) and 2% by weight of zinc dodecylbenzenesulfonate, calculated on the tallow. The content of the reactor was heated to 230° C. and 600 l of ammonia per kilogram of fat per hour were passed through the mixture. The temperature was maintained for 3 hours at 230° C. and then raised to 260° C. within 1.5 hours. After 4.5 hours the glycerol discharged was terminated and about one half of the crude fatty nitrile had been discharged. At this time of the reaction the throughput of ammonia was reduced to 60 liters per kilogram of reaction mixture per hour and simultaneously the reaction temperature was raised to 290° C. During the temperature increase the glycerol-containing crude nitrile was washed with water and the nitrile freed from glycerol was recycled into the reactor heated to 290° C. After a reaction period of 6.5 hours altogether (after-reaction 2 hours) the tallow nitrile was discharged and freed from the catalyst by distillation. 417 g (93.2%) of tallow nitrile having an amide content below 0.05% by weight and an acid number of 0.1 and 42.9 g (82.7%) of pure glycerol (according to the hydroxyl number) were obtained.

EXAMPLE 17

The apparatus described in Example 16, was charged with 500 g of industrial grade tallow (saponification number 191.4, acid number 1.5) and 2% by weight of zinc dodecylbenzenesulfonate, calculated on the tallow. During the course of the reaction, 600 l of ammonia per kg of fat per hour were passed through the reaction mixture, while the temperature was maintained for 3 hours at 230° C. and then raised to 280° C. within 2.25 hours. The total reaction time was 5.25 hours. During the reaction care was taken that the temperature gradient between the bottoms and the transition was as low as possible. The condensate obtained was separated by a water wash into crude fatty nitrile and glycerol.

The isolated 432.8 g of crude fatty nitrile (amide content 6.1% by weight) were introduced into a reactor provided with gas inlet tube, stirrer, internal thermometer and condensation system and 2% by weight of zinc dodecylbenzenesulfonate were added. 60 l of ammonia per kg of reaction mixture per hour were passed through at 290° C., while the reaction water formed was discharged. The reaction time was 1 hour. After distillation of the reactor content, 415 g (93.1%) of tallow nitrile having an amide content below 0.05% by weight and an acid number of 0.1 and 47.3 g (91.2%) of pure glycerol (according to hydroxyl number) were obtained.

EXAMPLE 18

500 g of industrial grade (saponification number 194.8, acid number 0.45) were treated according to the method of Example 17 but with catalysts given in the table below. The following results were obtained:

| Catalyst | reaction time (hr) | nitrile yield crude nitrile (%) | nitrile yield after treatment (%) | yield of crude glycerol (%) |
|---|---|---|---|---|
| cadmium octadecyl-benzenesulfonate | 5.25 | 95.5 | 93.3 | 82 |
| cobalt n-octanesulfonate | 5.5 | 95 | 92.8 | 75.2 |
| zinc toluene-2.4-disulfonate | 6 | 85 | 82.5 | 71 |
| zinc 2.5-dimethyl-benzene-sulfonate | 4.5 | 94.3 | 92.1 | 80.5 |
| lead 2-methyl-benzoate | 6.25 | 91.2 | 90 | 70 |
| zinc 3-dodecyl-benzoate | 5.75 | 91.8 | 89.7 | 75.3 |
| zinc caprylate | 6 | 89 | 87.4 | 73.4 |
| zinc erucate | 5.75 | 92.6 | 90.2 | 78.6 |

EXAMPLE 19

The reaction was carried out in a heatable reactor having a capacity of 1000 cm$^3$, provided with gas inlet tube, stirrer, internal thermometer, and a receiver system with a gas outlet. An amount of triglyceride or monoglyceride, as given in the table below, together with 2% by weight of a catalyst, as specified in the table, were introduced into the reactor. During the reaction 600 l of ammonia per kg glyeride per hour were passed through the reaction mixture. A temperature of 230° C. was maintained for three hours and then raised in a rate of 10° C. after each half an hour. At a temperature of 270° C. the reaction was terminated. The condensed product mixture was separated by water extraction at a temperature of between 80° and 90° C. into a fatty acid nitrile and a glycerol/water phase. The content of amide and fatty acid of the nitrile so obtained together with the nitrile yield and the yield of crude glycerol are given in the table below. The isolated fatty acid nitriles were introduced into a reactor provided with gas inlet tube, stirrer, internal thermometer and condensation system and 1% by weight of zinc dodecylbenzenesulfonate were added. 150 l of ammonia per kilogram reaction medium per hour were passed through the reaction mixture at a temperature of 290° C.

The water of reaction was discharged with the gas current. After two hours the reaction was terminated. The reaction products were then distilled. The nitriles had a fatty acid content of about 0.1% by weight and an amide content of about 0.2% by weight.

| glyceride | catalyst (% b.w.) | nitrile reaction time (hr) | yield (%) | a-mide content (%) | fatty acid content (%) | nitrile from after-treatment (%) | crude glycerol |
|---|---|---|---|---|---|---|---|
| 481 g castor oil | 2% zinc dodecyl-benzene-sulfonate | 10 | 93.6 | 6.8 | 2.6 | 91.9 | 96 |
| 485 g butter fat | 2% zinc dodecyl-benzene-sulfonate | 5.2 | 90.4 | 15.2 | 1.4 | 87.2 | 92 |
| 441 g glycerol mono-oleate | 2% zinc dodecyl-benzene-sulfonate | 5.25 | 86.8 | 10 | 1.3 | 82 | 88 |
| 500 g industrial grade tallow | 2% zinc isopalmitate | 6.5 | 93.5 | 12 | 0.7 | 91 | 62 |

EXAMPLE 20

In the reaction apparatus described in Example 19 480 g tristearin and 2% by weight of zinc-stearate, calculated on the glyceride, were introduced. The reaction was performed by passing 600 l of ammonia per kg of glyceride per hour through the reaction mixture. The temperature was 250° C. After the reaction time of 4.5 hours the volatile reaction products were discharged into the receiver system. The product mixture was separated into a nitrile and a glycerol/water phase. The nitrile had an amide content of 6.2% by weight and a fatty acid content of 1.5% by weight. The yield of stearic nitrile was 90% and of pure glycerol 81%. The nitrile was subjected to an aftertreatment and a distillation as described in Example 19. The nitrile yield was then 87.6%, the nitrile having an amide content of 0.2% by weight and a fatty acid content of 0.2% by weight.

What we claim is:

1. A process for producing simultaneously glycerol and saturated or olefinically unsaturated fatty acid nitriles without isolating intermediates by treating fatty acid glycerides or mixtures of fatty acid glycerides with gaseous ammonia at elevated temperatures in the presence of catalysts, wherein the improvement comprises contacting the liquid fatty acid glyceride at temperatures of from about 220° to about 300° C. with a flow of at least 200 liters ammonia per kilogram of fatty acid glyceride per hour in the presence of metal salt of a carboxylic or sulfonic acid as a catalyst, wherein in said metal salt the metal cation is lead, cadmium, iron, cobalt, zinc, tin, titanium, zirconium, chromium, antimony, manganese, or nickel and the anion is selected from the group consisting of saturated aliphatic mono- and polycarboxylic acids; olefinically unsaturated aliphatic mono- and polycarboxylic acids; mono-, di-, and trialkylated benzene and naphthalene mono- and polycarboxylic acids; alkane mono- and disulfonic acids; fluorosubstituted alkane monosulfonic acids; monohydroxy-substituted alkane monosulfonic acids; mono-, di-, and trialkylated benzene- and naphthalene- mono- and polysulfonic acids; and (monocarboxy)alkyl and (dicarboxy)alkyl benzene and naphthalene mono- and polysulfonic acids; or mixtures of said catalysts; removing a product mixture containing said nitriles, glycerol, and water formed from the liquid fatty acid glycerides, and subjecting the product mixture to a phase separation into a nitrile phase and a glycerol/water phase.

2. The process as claimed in claim 1, wherein said glycerides are vegetable or animal fats and oils.

3. The process as claimed in claim 1, wherein said glycerides are tri-, di-, and monoglycerides of the formula

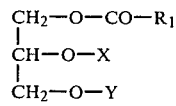

wherein X is H or CO—$R_2$; Y is H or CO—$R_3$, and $R_1$, $R_2$, $R_3$, are selected from the group consisting of
(a) alkyl radicals containing from 3 to 23 carbon atoms;
(b) olefinically unsaturated aliphatic hydrocarbon radicals containing from 3 to 23 carbon atoms and having from 1 to 6 isolated or conjugated double bonds;
(c) monohydroxy-substituted alkyl radicals containing from 3 to 23 carbon atoms;
(d) monohydroxy-substituted olefinically unsaturated aliphatic hydrocarbon radicals containing from 3 to 23 carbon atoms and having from 1 to 6 double bonds.

4. The process as claimed in claim 1, wherein the temperature is raised from about 220° C. at the beginning of the reaction to about 300° C. at the end of the reaction.

5. The process as claimed in claim 1, which comprises maintaining a temperature level in the range of from about 220° to about 240° C. until between 30 and 70 percent of the theoretical amount of glycerol is removed, then raising the temperature over a period from about 0.5 to about 5 hours to a temperature level in the range of from about 270° to about 300° C. and completing the reaction.

6. The process as claimed in claim 1, which comprises subjecting fatty acids and fatty acid amides contained in said product mixture as by-products to an aftertreatment with ammonia prior to or following the phase separation.

7. The process as claimed in claim 1, which comprises removing the product mixture by means of fractionated distillation, whereby recycling fatty acids and fatty acid amides contained in said product mixture as by-products, and then subjecting the product mixture to the phase separation.

8. A process for producing simultaneously glycerol and saturated or olefinically unsaturated fatty acid nitriles without isolating intermediates by treating fatty acid glycerides or mixtures of fatty acid glycerides with gaseous ammonia at elevated temperatures in the presence of catalysts, wherein the improvement comprises contacting the liquid fatty acid glyceride at temperatures of from about 220° to about 300° C. with a flow of at least 200 liters ammonia per kilogram of fatty acid glyceride per hour in the presence of metal salt of a carboxylic or sulfonic acid as a catalyst, wherein in said metal salt the metal cation is lead, cadmium, iron, cobalt, zinc, tin, titanium, zirconium, chromium, antimony, manganese, or nickel and the anion is selected from the groups consisting of saturated aliphatic mono- and polycarboxylic acids; olefinically unsaturated aliphatic mono- and polycarboxylic acids; mono-, di- and trialkylated benzene and naphthalene mono- and polycarboxylic acids; alkane mono- and disulfonic acids; fluoro-substituted alkane monosulfonic acids; monohydroxy-substituted alkane monosulfonic acids; mono-, di-, and trialkylated benzene and naphthalene mono- and polysulfonic acids; and (monocarboxy)alkyl and (dicarboxy)alkyl benzene and naphthalene mono- and polysulfonic acids; or mixtures of said catalysts; removing a part of the product mixture containing substantially the entire amount of glycerol and a proportional portion of water and of the nitrile formed from the liquid fatty acid glycerides, subjecting said part of the product mixture to a phase separation into a nitrile phase and a glycerol/water phase, water-extracting and combining the separated nitrile phase with the unremoved nitrile portion and treating said combined nitriles with a flow of ammonia of from about 5 to about 150 liters ammonia per kilogram nitrile per hour at temperatures of from about 200° to about 320° C. in the presence of said catalysts defined hereinbefore.

9. The process of claim 1 or 8, wherein said cation of the metal salt catalyst is lead, cadmium, iron, cobalt, and zinc; and wherein the anion is selected from the group consisting of
(a) alkanemonosulfonic acids, monohydroxyalkanesulfonic acids, and fluoro-substituted alkanesulfonic acids, having from 4 to 24 carbon atoms;
(b) mono-, di-, and trialkylated benzene- and naphthalene-mono- and disulfonic acids, containing alkyl radicals of from 1 to 24 carbon atoms; and
(c) (monocarboxy)monoalkyl and (dicarboxy)monoalkyl benzene and naphthalene mono- and disulfonic acids, containing alkyl radicals of from 1 to 26 carbon atoms.

* * * * *